United States Patent [19]
Affleck et al.

[11] Patent Number: 5,799,682
[45] Date of Patent: Sep. 1, 1998

[54] REDUCTION OF DIFFUSIONAL DEFOCUSING IN HYDRODYNAMICALLY FOCUSED FLOWS

[75] Inventors: Rhett L. Affleck, Lawrenceville, N.J.; James N. Demas, Charlottesville, Va.; Peter M. Goodwin, Jemez Springs; Richard Keller, Los Alamos, both of N. Mex.; Ming Wu, Middle Island, N.Y.

[73] Assignee: The Regents of the University of California, Los Alamos, N. Mex.

[21] Appl. No.: 758,738

[22] Filed: Dec. 6, 1996

Related U.S. Application Data

[60] Provisional application No. 60/020,679 Jul. 1, 1996.
[51] Int. Cl.$^6$ .................................................. F15C 1/20
[52] U.S. Cl. .................. 137/14; 137/567; 137/806; 137/828
[58] Field of Search ........................ 137/566, 567, 137/828, 806, 807, 14

[56] References Cited

U.S. PATENT DOCUMENTS

| | | | |
|---|---|---|---|
| 3,123,285 | 3/1964 | Lee | 137/807 |
| 3,334,641 | 8/1967 | Bjornsen | 137/828 |
| 3,548,851 | 12/1970 | Sampson | 137/807 |
| 5,637,208 | 6/1997 | Dourdeville | 137/567 |
| 5,641,006 | 6/1997 | Autrey et al. | 137/101.19 |

*Primary Examiner*—A. Michael Chambers
*Attorney, Agent, or Firm*—Ray G. Wilson

[57] ABSTRACT

An analyte fluid stream with first molecules having relatively low molecular weight and a corresponding high coefficient of diffusion has reduced diffusional defocusing out of an analyte fluid stream. The analyte fluid stream of first molecules is associated with second molecules of relatively high molecular weight having a relatively low coefficient of diffusion and a binding constant effective to associate with the first molecules. A focused analyte fluid stream is maintained since the combined molecular weight of the associated first and second molecules is effective to minimize diffusion of the first molecules out of the analyte fluid stream.

9 Claims, 3 Drawing Sheets

REDUCTION OF DIFFUSIONAL DEFOCUSING IN HYDRODYNAMICALLY FOCUSED FLOWS

This invention was made with government support under Contract No. W-7405-ENG-36 awarded by the U.S. Department of Energy. The government has certain rights in the invention.

This application claims the benefit of provisional application Ser. No. 60/020,679 filed Jul. 1, 1996.

BACKGROUND OF THE INVENTION

This invention relates to merging flow streams, and, more particularly, to reducing diffusion of an analyte out of a merging flow stream containing the analyte.

Several groups have developed the capability to detect single fluorescent molecules in solution as they flow through a focused laser beam. To accomplish this feat, the fluorescence of a single molecule must be discriminated from background emission associated with the solvent. This background emission arises from luminescent impurities and Rayleigh and Raman scattering.

Very small detection volumes are often used to reduce the contribution of background emission. The detection volume is the illuminated volume in the field of view of the detector. Careful attention to experimental details can result in a detection volume on the order of a picoliter. For efficient detection, most of the molecules in the sample must pass through the detection volume. Hydrodynamic focusing is widely used in flow cytometry and related techniques to form sample streams a few microns in diameter that pass through the center of the focused excitation laser beam where the irradiation is most uniform.

When low molecular weight analytes such as fluorescent dyes or fluorescent tagged nucleotides are used, radial diffusion of particles out of the focused sample stream can become a serious source of defocusing. FIG. 1 shows how diffusion of a low molecular weight analyte sample stream 10 into a surrounding sheath fluid 12 can occur and cause a significant fraction of analyte 15 to miss detection volume 14, defined by the intersection of focused light beam 16 and sample stream 10. For single molecule detection (SMD) by luminescence, such as in single molecule DNA sequencing, any loss of analyte molecules can seriously degrade the efficiency of detection or sequencing. For sample stream 20, the diffusion of high molecular weight analytes 21 into a sheath fluid 22 is much slower and results in small or negligible loss of analyte 21, as shown in FIG. 2.

Further, molecules that pass through the edges of the detection volume result in a smaller number of detected photoelectrons. It is only when most of the molecules pass through the center of the detection region, i.e., a tightly focused sample stream, that the magnitude of the fluorescence signal from each molecule is similar and the signal from single molecules can be distinguished from the background easily; this can result in detection efficiencies greater than 90%. Constant amplitude signals are also important when it is desirable to distinguish among different analyte molecules by the magnitude of the photoelectron burst associated with each molecule.

To put this into perspective, the diffusion coefficient of the common fluorescent tag TRITC (tetramethyl rhodamine isothiocyanate) is 300 $\mu m^2$/sec. In a typical experiment, the sample might have 50 ms to diffuse before reaching the analysis region. This causes a diffusional spreading of a 2 $\mu m$ diameter stream to a mean diameter of 17 $\mu m$. Since the analysis laser beam may be only 10 $\mu m$ in diameter, a significant fraction of the analyte species can either miss the detection volume or be sampled with lower efficiency.

Another advantage of having a tightly focused sample stream that does not broaden appreciably is that it now becomes possible to interrogate the sample stream at different positions along its length with multiple laser beams. If these beams are different colors, multiple analyses of different species becomes possible. If single color laser beams are used, coincidence detection of a species after the correct time delay in a second laser beam located downstream of a first laser beam can be used to verify that a fluorophore seen in the first laser beam was indeed there. Such multiple laser beam arrangements are also useful for kinetics measurements at the single molecular species level. In the absence of sustained focusing, the working distance for the multiple analysis beams becomes very short, which greatly complicates or precludes such coincidence measurements or multicolor analysis.

The use of high flow velocities to reduce radial diffusion is an attractive approach. To some extent, the reduction in the number of photons detected from a single molecule due to the reduced residency time of a molecule in the detection volume can be compensated for by increasing the excitation laser intensity. However, optical saturation and nonlinear photobleaching introduce an upper limit to the laser power that can be used effectively. Laser powers in excess of the saturation limit result in larger background signals but not larger analyte signals.

Reduction of axial diffusion becomes important when it is necessary to maintain the order of analyte molecules such as in single molecule DNA sequencing. At low flow rates, the order of analyte molecules introduced into the flow stream can be perturbed by axial diffusion. Elimination of axial diffusion becomes even more important when low flow rates are used to increase the number of photons from each molecule.

Another problem that can arise in flow cytometry is photochemical instability and low luminescence yield for the analyte molecules. The lower the luminescence yield, the more difficult it is to acquire enough photons for adequate signal-to-noise ratio. Similarly, the higher the photochemical decomposition yield, the fewer photons that can be emitted before photodecomposition and, thus, the poorer the signal-to-noise ratio.

The problems caused by diffusion of small molecules in a sample flow stream are addressed by the present invention. Accordingly, it is an object of the present invention to reduce the radial and axial diffusion of analyte molecules in a sample flow stream.

It is another object of the present invention to maintain a tightly focused analyte flow stream along an axial path for the flow stream.

Yet another object of the present invention is to maintain an ordered flow of analyte molecules along an axial path.

One other object of the present invention is to enhance the luminescence yield and photochemical stability.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, this invention may comprise a method for reducing diffusional defocusing of first molecules having a low molecular weight and a corresponding high coefficient of diffusion out of an analyte fluid stream containing the first molecules. The first molecules are associated with second molecules having a relatively high molecular weight and corresponding low coefficient of diffusion. In a particular embodiment, the analyte fluid stream of first molecules is surrounded with a sheath fluid containing second molecules of relatively high molecular weight having a relatively low coefficient of diffusion in the sheath fluid and effective to associate with the first molecules. A focused analyte fluid stream is maintained since the effective molecular weight of the associated first and second molecules is effective to minimize diffusional defocusing of the first molecules out of the analyte fluid stream.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

In accordance with our invention, the addition of a suitable high molecular weight polymer molecule to a sheath or analyte flow stream causes a high molecular weight complex to form between a small analyte molecule and the relatively higher molecular weight polymer. This high molecular weight association greatly reduces or even essentially eliminates both radial and axial diffusional defocusing and mixing of the analyte molecule in the complex. Also, in favorable cases, this complex association can have a significantly increased luminescence yield and increased photostability compared to the unassociated analyte molecule.

Many high molecular species will associate with low molecular weight compounds with high affinity. As used herein, the "association" of the analyte and the polymers can be by electrostatic attraction, hydrophobic-shape attraction, and hydrogen bonding. Polyelectrolytes with oppositely charged analytes are an example of electrostatic binding. Cyclodextrins and calixarenes are an example of shape-hydrophobic interactions. Proteins, enzymes, polymerized dendrimer particles, and DNAs are examples of systems that show hydrogen bonding, shape, charge, and hydrophobic interactions. Indeed, in many cases, more than one interaction may contribute to binding.

With reference to FIGS. 3A and 3B, our improvement is to place in the sheath flow stream 36 or analyte flow stream 38 or 40, respectively, a high molecular weight species 32 in a proximity to associate strongly with analyte 34 in a flow stream 38 or 40. Then, analyte 34 encounters and associates with the high molecular weight species 32 (also referred to as an anchor). The new association complex 42 then has a molecular weight equal to the sum of that of both species, and composite molecule 42 has substantially reduced diffusion. In effect, low molecular weight analyte 34 assumes the molecular weight of the slowly diffusing anchor 32, shown in FIGS. 3A and 3B. This approach is perfectly general and requires a high molecular weight anchor that is soluble in the fluid that carries analyte 34, has a strong and rapid association with the analyte molecule, and does not adversely affect the fluorescence properties of the analyte on binding. The precise association or binding mechanism is irrelevant.

Assuming a tight association, substantial reduction in diffusional defocusing does not require exceptionally high molecular weight anchors. Since diffusion coefficients are roughly inversely proportional to the 0.4 power of the molecular weight, an increase of 100 in molecular weight (e.g., a 50,000 MW polymer associated with a 500 MW dye) would reduce the mean diffusion distance by a factor of 2.5. This yields an enormous improvement in detection efficiency and working distance for multi-laser beam analysis systems and the capability to use much lower flow rates with the concomitant larger number of detected photons.

Several different systems that use associational molecular weight enhancement to decrease diffusional defocusing are illustrated below. Examples include electrostatically stabilized association as well as nonspecific, possibly hydrophobic, interactions. In addition, substantial enhancement of the fluorescence intensity of the dye on association was demonstrated for an exemplary system. While the following examples introduce the high molecular weight anchors in a sheath fluid surrounding the fluid stream containing the analyte molecules, the anchor molecules could be introduced directly into the analyte flow stream to associate with the analyte molecules.

Interactions based on electrostatic attraction between charged dyes and polyelectrolytes, as well as a nonspecific interaction between poly(vinyl-pyrrolidone) (PVP) and anionic fluorescein dyes, were investigated. There are a variety of high molecular weight polymers with large numbers of cations or anions covalently attached to the polymer backbone (polyelectrolytes). If the small target analyte is a charged species, it can associate strongly with a polyelectrolyte anchor of the opposite overall charge.

The stabilization here is largely ionic, but specific polymer analyte interactions could act to enhance the stability. For example, poly(methylacrylic) acid shows strong shape-dependent associations where the shape is controlled by pH. For nonionic binding, poly(vinyl-pyrrolidone) (PVP) and anionic fluorescein dyes were chosen. For the PVP systems, substantial enhancement of the fluorescence intensity of the dye upon association has been shown. Regardless of the associational mechanism, once complexed the analyte assumes diffusion properties similar to the polymer.

Experimental Section

Chemicals and Reagents: Water was deionized and purified on a Milli-Q Water System (Millipore). Dulbecco's phosphate-buffered saline (1×, without calcium or magnesium, D-PBS, pH 7.4) was from GIBCO. High purity methanol was obtained from Baxter. Tetramethylrhodamine isothiocyanate (TRITC) was from Molecular Probes. Rose Bengal (Aldrich), Eosin Y (Aldrich), fluorescein (Exciton Chemical Co.) were used without purification.

Poly(vinyl-pyrrolidone) (K90, MW 360,000) [PVP], was from GAF Corp. (New York, N.Y.). Poly(2-vinyl-1-methylpyridinium) bromide (MW 50,000) [PMePyBr], poly (styrenesulfonic acid) sodium salt (MW 500,000) [Na(PSS) ], poly(2-methacryloxyethyltrimethylammonium bromide) (200,000 MW) [PMACRBr], dextran sulfate, sodium salt (MW 500,000), poly(acrylic acid) sodium salt (MW 225,000) [NaPAA], and (diallyl dimethyl ammonium chloride) (200,000 MW) were all from Polysciences, Inc.

Figure 1:
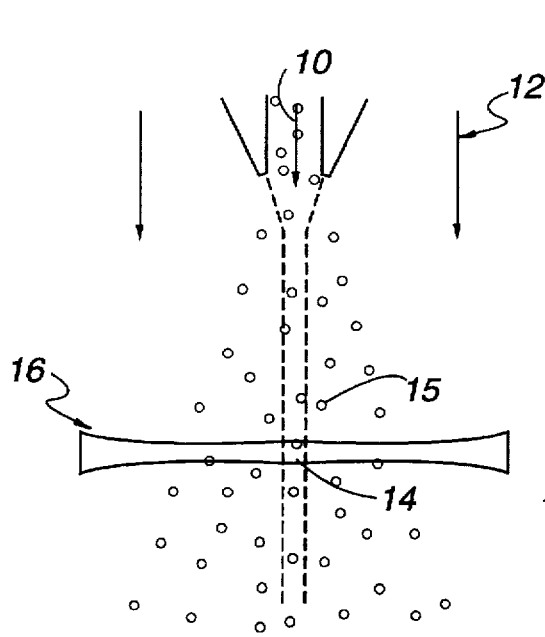
FIG. 1 pictorially depicts analyte molecule diffusion with conventional sheath flow for small analyte molecules.
Figure 2:
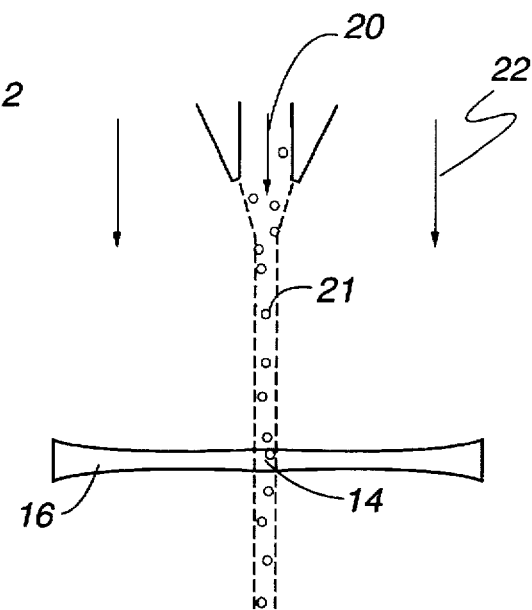
FIG. 2 pictorially depicts reduced analyte molecule diffusion with conventional sheath flow for large analyte molecules.
Figure 3A:
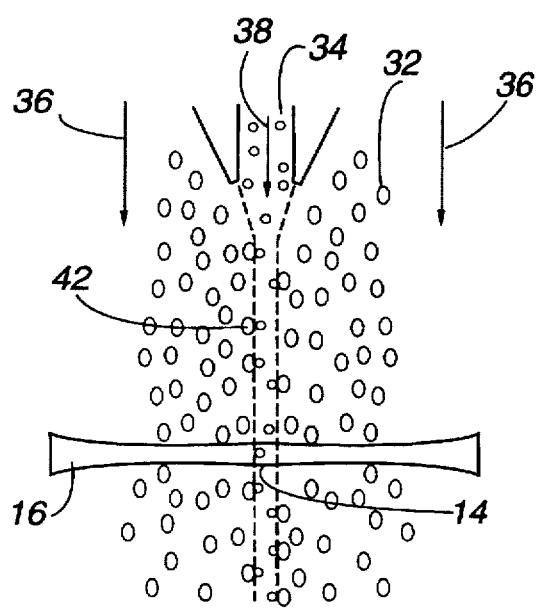
FIGS. 3A and 3B pictorially depict the reduction of small analyte molecule diffusion when associated with large molecules.
Figure 3B:
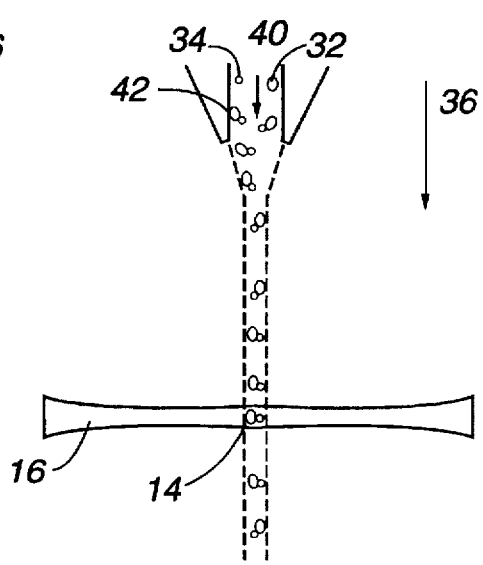
Figure 4:
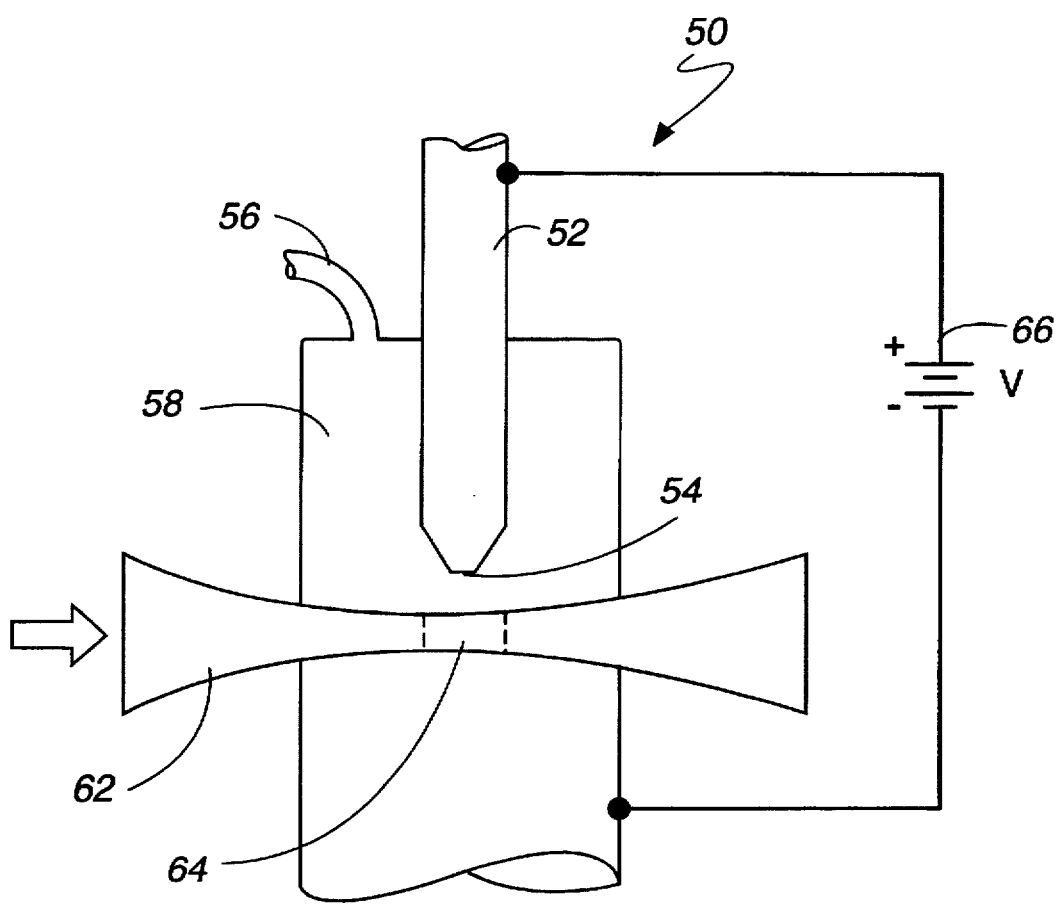
FIG. 4 is a pictorial illustration of experimental apparatus used to obtain the experimental results discussed herein.

Sheath Flow Apparatus: FIG. 4 is a pictorial illustration of apparatus 50 used for these experiments. A sample fluid containing analyte molecules is delivered through capillary tube 52, which may be 20–100 μm inside diameter (i.d.) and terminates in an outlet 54 with a reduced diameter, e.g., 1–50 μm i.d. The outlet may be tapered or blunt. A sheath fluid is introduced through inlet 56 into conventional sheath flow cell 58, which may be a square bore tube having an internal wall dimension of about 250 μm. The sheath fluid is introduced by gravity flow, a syringe pump, or other suitable pump. In the present experiments, a dye laser beam 62 (554 nm) was used as the excitation source and was focused by conventional optics to irradiate a small volume in the center of cell 58 that forms measurement volume 64. Sample fluorescence was conventionally collected with a 40×, 0.85 NA microscope objective and imaged onto the focal plane of a CCD video camera (not shown) As shown in FIG. 4, analyte dyes were delivered by electrokinetic flow with an applied voltage 66, which may be 0–1500 V, between capillary 52 and sheath flow cell 58. The analyte flow may also be introduced by pressure/gravity flow, syringe pump, or the like, and the choice is not critical, as noted above.

In accordance with our invention, high molecular weight molecules are associated with the analyte molecules to maintain a focused stream of analyte molecules between capillary outlet 54 and measurement volume 64. As used herein, "pump" means any suitable mechanism for moving fluid, e.g., pressure/gravity flow, syringe pump, and the like. An analyte may be introduced into capillary tube 52 by pump 72 and sheath fluid 84 introduced into sheath flow cell 58 by pump 82. In a first embodiment, high molecular weight molecules 78 are introduced into capillary 52 by pump 76. In a second embodiment, high molecular weight molecules 88 are introduced into sheath flow cell 58 by pump 86.

Visualization of Focusing: Focusing was studied by two methods. One method examined the persistent hydrodynamic focusing of a dye in a fluorescence flow cell with the sheath fluid containing electrolyte and the anchor polymer. The sample was introduced from a small capillary in the center of a 250 μm square bore sheath flow cuvette. The sample introduction capillaries were formed by pulling 90 μm o.d., 20 μm i.d. fused silica capillaries (Polymicro Technologies, Inc., Phoenix, Ariz.) to yield 1–5 μm tips. The cell and delivery system were similar to that described above; either electrokinetic or pressure introduction of the dye through the capillary was used. There was no difference in behavior between the two methods of sample introduction. The properties of the sample stream were visualized by placing the cell under a Zeiss Axioplan fluorescence microscope with a mercury arc excitation. Sheath fluid was introduced with a syringe pump (Harvard Apparatus, South Natick, Mass.). Sample flow was across the field of view. Complementary excitation-emission filters were used to excite and visualize the fluorescence. Visualizations of the diameter of the sample stream as a function of distance from the capillary were obtained from photographs of the sample stream.

Quantitative sample stream diameter measurements were made using the apparatus shown in FIG. 4. Fluorescence was excited by a dye laser tuned to 554 nm and focused to a beam waist of 15 μm ($e^{-2}$ diameter) in the center of the flow channel. The CCD video camera output was recorded with a VCR for subsequent processing. The intersection of the laser beam and the sample stream was viewed rather than the entire spatial evolution of the stream. However, since the size and distribution of this image determines the efficiency of SMD, this technique provides information not easily available from the fluorescence microscope. To quantitate the images, they were digitized and processed with NIH Image. The widths of the fluorescence images were measured as the full width of the 1/e points.

Luminescence Titrations: Fluorescence titration curves were acquired on a spectrofluorimeter. A known volume of the dye in an appropriate buffer was placed in the fluorimeter cuvette. The emission spectrum was measured. Aliquots of a concentrated polymer solution made up in a dye-buffer solution identical to the sample in the cuvette were added. The solution was thoroughly mixed and a new spectrum was measured. The equilibrium was assumed to be

where A is the analyte (dye), P is the polymer, and $K_{eq}$ is the equilibrium binding constant. The polymer concentration was expressed in weight percent, which gave $K_{eq}$ in units of wt %$^{-1}$. $K_{eq}^{-1}$ is then the wt % of polymer that binds 50% of the dye.

Assuming that exchange is slow on the time scale of the excited state lifetime, the fluorescence intensity, F, as a function of polymer concentration, is given by $$F = \frac{F_\infty K_{eq}[P] + F_0}{1 + K_{eq}[P]} \quad (1)$$

where $F_0$ and $F_\infty$ are the fluorescence intensity in the absence of polymer and at infinite polymer concentration (i.e., all dye bound) and [P] is the polymer concentration. Titration curves were fit by nonlinear least squares. In general, since $F_0$ is well defined, this quantity was set at the fluorescence intensity before the first addition of polymer. All of the binding data are fit quantitatively by this approach.

For quenching studies, data were fit to normal Stern-Volmer quenching kinetics $$F_0/F = 1 + K_{SV}[Q] \quad (2)$$

where $F_0$ is the emission intensity in the absence of quencher, F is the intensity with quencher, [Q] is the quencher concentration, and $K_{SV}$ is the Stern-Volmer quenching constant. Depending on whether quenching is static (associational) or diffusional, $K_{SV}$ is either the association constant or $k_2 \tau_0$, where $k_2$ is the bimolecular quenching constant and $\tau_0$ is the excited state lifetime in the absence of quencher.

Viscosity Measurements: Viscosity measurements were made using a conventional Ostwald viscosimeter. Water was used as the reference.

Results

Cationic dyes with anionic polymers: Initially, using the fluorescence microscope, the positively charged TRITC was used as the analyte in D-PBS buffer (1×) with the anionic polymers at 0.1 wt %. It was clear that Na(PSS) dramatically reduced defocusing. Dextran sulfate had a significant effect, but not as much as the Na[PSS]. There was no discernible effect with Na[PAA]. The Na[PAA] was probably completely protonated at the pH (~7) used, which would effectively neutralize the negative charge on the polymer. This would negate electrostatic attraction and minimize or eliminate association. Further work with anionic polymers was limited to the PSS system.

TRITC (1 μM in 1× D-PBS buffer) was introduced electrokinetically as the analyte with 0.001 wt % Na[PSS] in the 1/100× D-PBS sheath fluid as shown in FIG. 4. Quantitative data for this system were obtained with the video camera with three different sheath flow rates (5, 25, and 100 μL/min) with and without 0.001 wt % Na[PSS]. The distance between the capillary introduction point and the center of the laser beam was 30 μm.

Reduction in diffusional defocusing was pronounced with the addition of even a small amount of polymer to the sheath flow stream. The sample stream diameter at the detection point was much narrower at 5 μL/min sheath flow rate with polymer than at 25 μL/min without the added polymer. Of course, diffusional defocusing is minimized at the higher flow rates, but for SMD a high flow rate is counterproductive because the reduced residency time in the detection volume reduces the number of photons that can be detected.

The sample stream width, taken from the digitizer, was found to vary as the reciprocal of the square root of the sheath velocity. When introducing a sample from a point source into a flowing sample stream of uniform velocity, the mean radial diffusion diameter, as viewed through the microscope, is related to V, which is the volumetric flow rate (μL/min), and diffusion coefficient D by $$\bar{x} \propto \sqrt{\frac{D}{V}}$$

Figure 5:
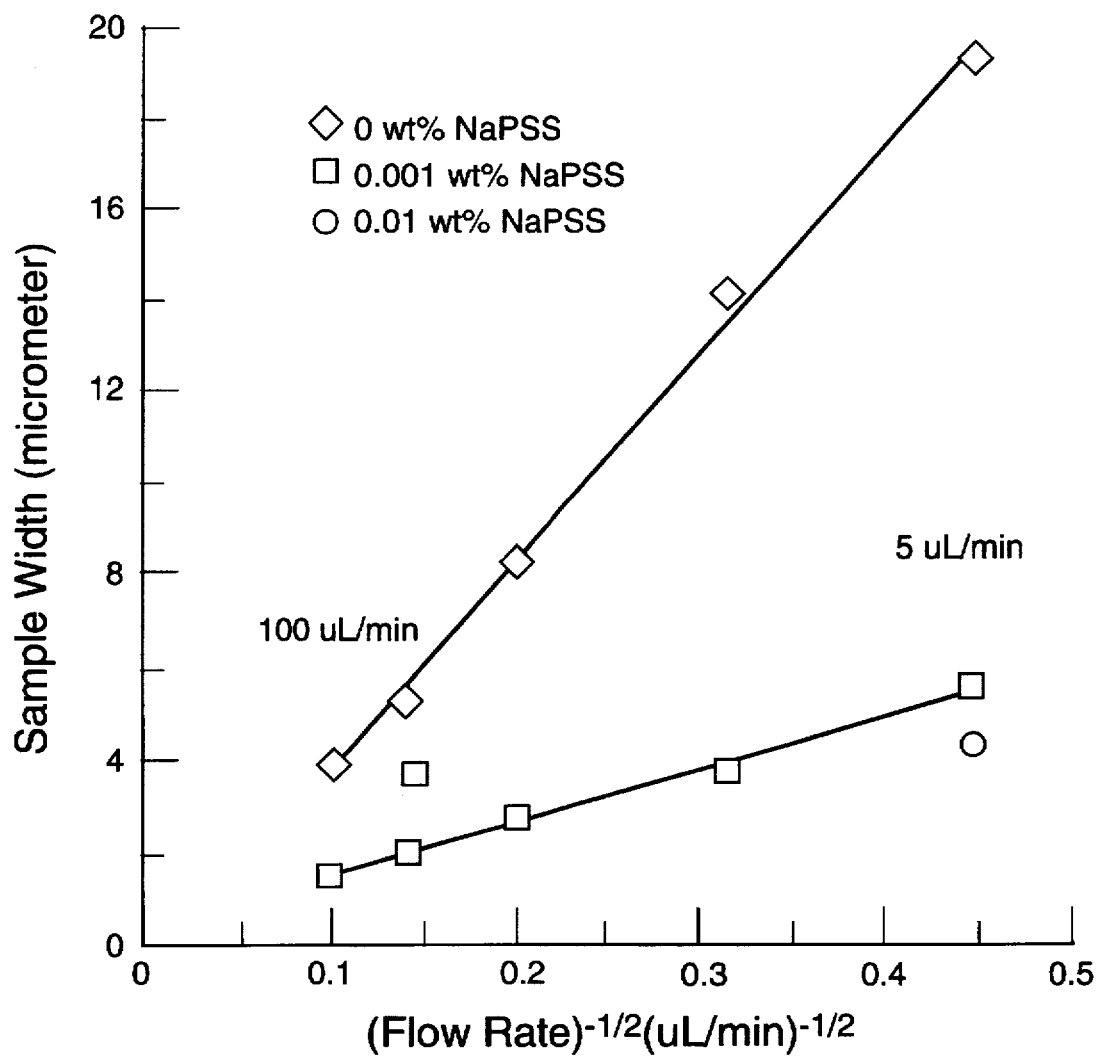
FIG. 5 graphically depicts the reduction in sample stream width when TRITC dye molecules are associated with a high molecular weight polymer Na[PSS]

FIG. 5 shows a plot of sample width versus $V^{-\frac{1}{2}}$ for the polymer free, 0.01 wt %, and 0.001 wt % solutions of Na[PSS]. The plots are linear as predicted by this simple theory. The ratio of the slope indicates that in Na[PSS], D is reduced by about a factor of 16. This would correspond to an effective increase in the molecular weight by a factor of 1000 based on the −0.4 power dependence of D on molecular weight. Such an increase would predict a molecular weight of the polymer-bound analyte on the order of half a million, which is similar to the 500,000 molecular weight of the Na[PSS]. These results indicate that virtually all of the analyte molecules are bound to, and diffuse with, the high molecular weight polymer.

Anionic Dyes with Cationic Polymers: Reduction in defocusing was not unique to cationic dye/anionic polymer combinations. The anionic fluorescein and the cationic PMACRBr polymer (0.04× D-PBS) exhibited strong sustained narrow sample streams as did anionic eosin with cationic poly(diallyl dimethyl ammonium chloride) at 0.1 wt % polymer. The reduction in defocusing was as good or better than for the TRITC/Na[PSS] system. $K_{eq}$ for fluorescein with PMACRBr was 620 (wt %)$^{-1}$. This corresponds to a 50% binding at less than 0.002 wt % of the polymer.

Another dye/polymer combination examined showed some of the complexities that can arise. Under the microscope, anionic fluorescein with 0.1 wt % [PMePy]Br revealed a very narrow sample stream that was only weakly luminescent. This was found to result from a strong excited state quenching of the fluorescein fluorescence by the polymer. In contrast to the other polymer systems that exhibited a plateau and nonlinear Stern-Volmer plots (expected for a binding system of Eq 1), the fluorescein/PMePyBr system gave a linear Stern-Volmer plot and no plateau. The Stern-Volmer quenching constant (0.04× D-PBS) was 12000 (wt %)$^{-1}$ or 50% luminescence quenching at 0.008 wt % polymer. The narrowness of the fluorescence imaging was probably due to essentially complete quenching of the dye as it diffused into the polymer-containing sheath fluid. While diffusion was certainly reduced, the absence of appreciable luminescence made this system of no practical value. It should be noted that these effects can be readily detected by routine experimentation.

Neutral Dyes with Polymers: Reduction of defocusing with a polymer was also demonstrated. Fluorescein, Rose Bengal, and eosin all showed strong focusing with PVP (0.4 wt %, 0.04× D-PBS). Also, as expected on the basis of the enhancement of luminescence intensity of bound versus free Rose Bengal, the PVP-associated Rose Bengal stream was visually much brighter than the PVP-free stream.

The luminescence of 10 μM Rose Bengal excited at 488 nm using a common laser beam both in the presence of 0.5 wt % PVP and without PVP showed that the polymer solution emission is much brighter than the polymer-free emission. For optimal excitation wavelengths, the Rose Bengal luminescence intensity is about a factor of 10 brighter in the presence of PVP compared to the polymer-free media. Since the fluorescence quantum yield of Rose Bengal in water is only about 1%, this large enhancement in PVP brings the fluorescence efficiency up to a value approaching that necessary for SMD, which was impractical with this fluorophore.

In contrast to Rose Bengal, there appeared to be no binding of TRITC with PVP.

Luminescence titration curves showed that the concentration of PVP necessary to bind 50% of eosin and Rose Bengal is approximately 0.005 wt %, demonstrating a reasonably tight and useful binding constant.

Non-Specific Polyion Effects: To exclude non-specific polyion effects, TRITC with 0.1 wt % 50,000 MW cationic PMePyBr was investigated. Electrostatic repulsion in this case minimizes ionic association; however, the polymer should have the same effect on ionic strength as the anionic polymer. No reduction in defocusing was observed for this poly-cation with TRITC. Thus, there is nothing unique about having a charged polymer in the sheath. The viscosity in this case is essentially the same as that of water.

DISCUSSION

The above results show that decreased dye defocusing in the presence of high molecular weight associating polymers is a general phenomena. It is present in all types of analyte/polymer combinations examined including cationic analytes with anionic polymers, anionic analytes with cationic polymers, and anionic analytes with neutral polymers. The only requirement is that the analyte associate strongly with the polymer at accessible polymer concentrations. Control experiments show that it is the association of the analyte with the high molecular weight polymer that is the critical parameter rather than viscosity changes or some non-specific effect of polyelectrolytes.

The methodology for reducing radial diffusion also assists in reducing axial diffusion, which becomes important when low flow rates are used to maximize detection sensitivity. This has importance in single molecule DNA sequencing, where the order of cleaved nucleotides is measured. Until this method of reducing radial and axial diffusion, very low flow rates coupled with high cleavage rates would cause the rate of DNA sequencing to be limited by axial diffusion misordering.

Binding in the oppositely charged systems is attributed to electrostatic binding. In the case of the neutral PVP, the associating mechanism is less clear. The increase in luminescence yield of Rose Bengal when bound is similar to luminescence yield increases on changing the solvent from water to more hydrophobic solvents. Thus, the binding environment is probably reasonably hydrophobic.

As one would expect, electrostatic binding is stronger than the non-specific or hydrophobic binding. In general, one might expect that systems based on electrostatic binding will give the tightest binding and, thus, the lowest useful polymer concentrations. A low polymer concentration will minimize background from adventitious luminescence impurities in the polymer.

It should be noted that the selected polymer must not contain groups that are capable of quenching the dye emission. If it does, the tight association merely enhances the intrinsic quenching.

An added advantage of PVP binding to fluorescein, eosin, and Rose Bengal is that it can greatly increase the fluorescence quantum yield and photochemical stability. In the case of Rose Bengal, the enhancement in luminescence yield is about an order of magnitude.

The above results show that polymer reduction of defocusing is a very general phenomena. It occurs with appropriate combinations of analyte and high molecular weight neutral or charged polymers. The only requirement is that strong analyte/polymer binding occur at the polymer concentration employed and that the luminescence not be adversely affected. While having opposite charges on the dye and polymer assists binding, it is certainly not required for binding and focusing as shown by the PVP results.

Many factors can be used to form high molecular weight complexes or to enhance the stability of complexes. Besides polyelectrolytes, a variety of guesthost systems can be employed to form association complexes. These include uncharged zwitterionic species that can associate via localized electrostatic interactions, water soluble ionomers that carry large hydrophobic regions, shape-selective polymeric cyclodextrin and calixarenes, charged and uncharged micelles that are stabilized by polymerization, water soluble block copolymer aggregates, polymerized dendrimer particles, polymeric size-shape selective crown ethers, charged and uncharged bilayer vesicles, and intercalation complexes such as DNA with planar dyes.

In addition, possible anchor species include biomolecules that would have a specific and strong association with the analyte. An example would be antibody/antigens where a large molecular weight antibody would stop diffusion of a low molecular weight hapten. Specific examples include antibodies that bind specifically to dyes such as fluorescein. A number of dyes can have binding affinities for pockets on proteins and, in many cases, fluorescence is enhanced by binding in these binding sites.

In addition, synthetic anchors may be created that would have specific and strong interactions with the analyte. Appropriate combinations of shape, size, charge, hydrogen bonding, and/or hydrophobic interactions would be selected to stabilize the association complex and further minimize the required concentration of anchor.

The methodology for reducing radial diffusion also assists in reducing axial diffusion where low flow rates are used to maximize sensitivity. By insuring that the sample stream is narrow enough, and by having an associating polymer in the sheath or sample stream, each fluorophore (e.g., tagged base in DNA sequencing) is guaranteed to react with a polymer within a short distance from sample introduction. By reducing molecular mobility, this association reduces both radial diffusion and axial diffusional misordering of the bases. Until this method of reducing axial diffusion, very low flow rates coupled with high cleavage rates were not an option.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for reducing the diffusion out of an analyte flow stream of first molecules having a relatively low molecular weight and corresponding high coefficient of diffusion out of said analyte flow stream, comprising the step of associating said first molecules with second molecules having a relatively high molecular weight and corresponding low coefficient of diffusion.

2. A method according to claim 1, including the step of selecting a high molecular weight polymer for said second molecules.

3. A method according to claim 2, wherein said high molecular weight polymer is selected from the group consisting of polyelectrolytes, cyclodextrins, calixarenes, proteins, enzymes, polymerized dendrimer particles, and DNA.

4. A method according to claim 1, including the step of selecting said second molecules to associate with said first molecules with electrostatic, shape, or hydrogen bonding affinities.

5. A method according to claim 4, wherein said first and second molecules, respectively, are cationic dyes and anionic polymers, anionic dyes with cationic polymers, and neutral dyes with polymers.

6. A method according to any one of claims 1 through 5, wherein the step of associating said first molecules with second molecules includes surrounding said analyte fluid stream of first molecules with a sheath fluid containing second molecules of relatively high molecular weight having a relatively low coefficient of diffusion in said sheath fluid and effective to associate with said first molecules.

7. A method according to any one of claims 1 through 5, wherein the step of associating said first molecules with second molecules includes introducing said second molecules into a capillary with said first molecules.

8. An analyte flow system for reducing the diffusion out of an analyte flow stream of first molecules having a relatively low molecular weight, said system comprising:

a capillary tube for forming said analyte flow stream with said first molecules to a small diameter;

a sheath fluid containing second molecules having a relatively high molecular weight and corresponding low coefficient of diffusion in said sheath fluid and effective to associate with said first molecules; and a flow tube for forming a sheath of said sheath fluid about said small diameter analyte fluid stream wherein said first molecules associate with said second molecules to reduce diffusion of said first molecules from said small diameter analyte fluid stream.

9. An analyte flow system for reducing the diffusion out of an analyte flow stream of first molecules having a relatively low molecular weight, said system comprising:

a capillary tube for forming said analyte flow stream with said first molecules to a small diameter;

a pump for introducing second molecules into said capillary with said first molecules, where said second molecules have a relatively high molecular weight and corresponding low coefficient of diffusion in a sheath fluid and effective to associate with said first molecules; and a flow tube for forming a sheath of said sheath fluid about said small diameter analyte fluid stream for movement of said analyte flow stream at said small diameter.

* * * * *